(12) United States Patent
Sato et al.

(10) Patent No.: US 8,466,694 B2
(45) Date of Patent: Jun. 18, 2013

(54) BIOMETRIC MEASUREMENT APPARATUS

(75) Inventors: Tomio Sato, Kita-ku (JP); Tadaaki Ishige, Shimotsuga-gun (JP)

(73) Assignee: Tanita Corporation, Itabashi-Ku, Tokyo (JP)

( * ) Notice: Subject to any disclaimer, the term of this patent is extended or adjusted under 35 U.S.C. 154(b) by 334 days.

(21) Appl. No.: 12/896,170

(22) Filed: Oct. 1, 2010

(65) Prior Publication Data

US 2011/0080181 A1     Apr. 7, 2011

(30) Foreign Application Priority Data

Oct. 2, 2009 (JP) ................. 2009-230632

(51) Int. Cl.
*G01R 27/28* (2006.01)
*A61B 5/05* (2006.01)

(52) U.S. Cl.
USPC ............ 324/692; 324/693; 600/547; 600/506

(58) Field of Classification Search
USPC ......... 600/547, 365, 384, 390, 386, 391–393, 600/481, 485, 490–492, 499–500, 504, 506, 600/385; 324/691, 692, 693, 704
See application file for complete search history.

(56) References Cited

U.S. PATENT DOCUMENTS

| | | | |
|---|---|---|---|
| 5,526,808 A | | 6/1996 | Kaminsky |
| 5,642,734 A | * | 7/1997 | Ruben et al. ................ 600/506 |
| 6,006,119 A | * | 12/1999 | Soller et al. ................ 600/322 |
| 6,766,191 B1 | * | 7/2004 | Billings et al. ............. 600/547 |
| 6,878,272 B2 | * | 4/2005 | Kawaguchi ............. 210/321.65 |
| 6,974,420 B2 | * | 12/2005 | Kaiser et al. ................ 600/554 |
| 2008/0195162 A1 | | 8/2008 | Lippert et al. |

FOREIGN PATENT DOCUMENTS

| EP | 0 417 796 A2 | 3/1991 |
|---|---|---|
| JP | 63-133062 | 6/1988 |

OTHER PUBLICATIONS

Lippert et al., US Application 2008/195162, Implantable Medical Device.*
Peretto et al., US Application 2009/0062665, Noninvasive Method and Apparatus for Measuring Blood Pressure by Determining a Maximum Frequency of Spectral Content of the Second Heart Sound.*
Search Report dated Jan. 21, 2011, issued by the European Patent Office in corresponding European Patent Application No. 10177797.7.

* cited by examiner

*Primary Examiner* — Huy Q Phan
*Assistant Examiner* — Dustin Dickinson
(74) *Attorney, Agent, or Firm* — Buchanan Ingersoll & Rooney PC (57) ABSTRACT

A biometric measurement apparatus has a measurement unit for measuring bioelectric impedance of different parts of a body and hematocrit. The measurement unit has impedance calculators (IPG1, IPG2) for measuring the impedance of tissues and blood of a living body with a first frequency to output as a first impedance (Z1), and for measuring the impedance of the tissues and blood of the living body with a second frequency to output as a second impedance (Z2), and has pulse wave analyzing units (MS1 and MS2) for analyzing differences of the first impedance between a first time and a second time and difference ($\Delta Z_H$) of the second impedance between the first time and the second time, and a hematocrit calculator (245) for calculating hematocrit based on the difference ($\Delta Z_L$) of the first impedance and the difference ($\Delta Z_H$) of the second impedance.

19 Claims, 7 Drawing Sheets

BIOMETRIC MEASUREMENT APPARATUS

BACKGROUND OF THE INVENTION

1. Field of the Invention

The present invention relates to a biometric measurement apparatus for generating an index showing the conditions of the blood in a living body, such as that of a human subject.

2. Description of Related Art

Hematocrit is an index showing the proportion of blood volume that is occupied by blood cells. In a case in which dialysis using an artificial kidney is performed, anemia is likely to occur because a hormone called erythropoietin, produced by the kidney, is abnormally low. For this reason, hematocrit is usually measured during dialysis for use as an index for diagnosing anemia.

During dialysis, a hematocrit measurement apparatus is provided at a blood path connecting a human body and an artificial kidney, thereby monitoring the hematocrit while performing dialysis.

Japanese Patent Application Laid-Open Publication No. 63-133062 discloses a hematocrit measurement apparatus for measuring the impedance at a high frequency and the impedance at a low frequency of the blood drawn from a human body, and for calculating the hematocrit based on the ratio therebetween.

However, this conventional hematocrit measurement apparatus requires the blood to be drawn from the human body to measure the hematocrit. Such an apparatus requires a patient to undergo a painful procedure of drawing blood, and the hematocrit is not something that can be readily measured at home.

SUMMARY OF THE INVENTION

The present invention has been made in view of the above and has as an object to provide an apparatus for measuring hematocrit without drawing blood from a human body.

The following description shows, in parentheses, reference numerals used for components of an embodiment corresponding to the elements of the present invention; however, these are merely examples and are not intended to limit the present invention to the corresponding elements.

To solve the above-described problems, a biometric measurement apparatus (1 or 2) according to the present invention has an impedance measurer (IPG1 and IPG2, or IPG) for measuring the impedance of tissues and blood of a living body with a first frequency, for output as a first impedance (Z1), and for measuring the impedance of tissues and blood of the living body with a second frequency, the second frequency higher than the first frequency, for output as a second impedance (Z2), the impedance measurer having output electrodes (220a and 220b) and input electrodes (230a and 230b) that are in contact with the surface of the body during the measurement; a first analyzing unit (MS1 or MS) for analyzing the variation of the first impedance, to output as a first variation amount ($\Delta Z_L$); a second analyzing unit (MS2 or MS) for analyzing the variation of the second impedance, to output as a second variation amount ($\Delta Z_H$); and an index generator (245 or 246) for generating an index indicating a component of the blood based on the ratio between the first variation amount and the second variation amount.

According to the present invention, an index indicating a component of blood can be generated without drawing blood from a human body. The focus is on the amount of variation in bioelectric impedance. The bioelectric impedance is obtained by measuring, from the surface of a human body, the impedance of a measurement area between different parts (two points) of the human body. Under the area being measured are tissues and blood. The blood periodically flows into the tissues in pulses. Therefore, the amount of blood that flows into the tissues varies. On the other hand, the impedances of the tissues themselves do not change. This is why the focus is on the amount of variation in bioelectric impedance, so that the effects of the tissues can be separated out. Blood can be broadly divided into blood plasma and red blood cells, for which the reactance components differ from each other. Therefore, the index indicating a component of blood can be calculated based on the ratio between the amount of variation (the amount of variation corresponding to a component of blood) of the first impedance measured with a first frequency and the amount of variation (the amount of variation corresponding to whole blood) of the second impedance measured by the second frequency that is higher than the first frequency. One such index is hematocrit.

Embodiments of the biometric measurement apparatus include a first embodiment in which the impedance measurer simultaneously executes a first process of measuring the first impedance with the first frequency and a second process of measuring the second impedance with the second frequency, and a second embodiment in which the impedance measurer executes the first process and the second process at different times. Since the amount of blood that flows into tissues can vary depending on the pulse period, measurement with higher accuracy is enabled according to the first embodiment. On the other hand, according to the second embodiment, the configuration can be simplified because one analyzing unit (MS) is used as the first analyzing unit and as the second analyzing unit.

In the second embodiment, the first analyzing unit may output, as the first variation amount, a first difference value that is the difference between the maximum value and the minimum value of the first impedance in one pulse period, and the second analyzing unit may output, as the second variation amount, a second difference value that is the difference between the maximum value and the minimum value of the second impedance in one pulse period. Alternatively, the first analyzing unit may perform frequency analysis of the first impedance, to output the intensity of the maximum spectrum corresponding to a pulse as the first variation amount, and the second analyzing unit may perform frequency analysis of the second impedance, to output the intensity of the maximum spectrum corresponding to a pulse as the second variation amount. The maximum spectrum corresponds to the fundamental wave component from among frequency components included in a pulse wave.

In the first embodiment, the impedance measurer may have a first frequency generator (211) for generating a first signal (S1) of the first frequency; a second frequency generator (212) for generating a second signal (S2) of the second frequency; a frequency multiplexer (213) for frequency-multiplexing the first signal and the second signal to obtain an output signal for supply to the output electrodes; a frequency separator (242) for demultiplexing an input signal obtained through the input electrodes into a third signal (S3) having the first frequency and a fourth signal (S4) having the second frequency; a first generator (IPG1) for outputting the first impedance based on the third signal; and a second generator (IPG2) for outputting the second impedance based on the fourth signal. In this case, the impedance with two different frequencies can be simultaneously measured by frequency-multiplexing.

In the first embodiment, regardless of whether performing frequency multiplexing, the first analyzing unit may preferably output, as the first variation amount, a first difference value that is the difference between the first impedance of a first time point and the first impedance of a second time point, and the second analyzing unit may preferably output, as the second variation amount, a second difference value that is the difference between the second impedance of the first time point and the second impedance of the second time point. In this case, because both the variation amount of the first impedance and the variation amount of the second impedance are the amount of variation from the first time and to the second time, it is possible to take measurements with higher accuracy.

Furthermore, in this case, the first impedance varies in synchronization with a pulse, the first time point may be a time point at which the first impedance is the minimum in one pulse period, and the second time point may be a time point at which the first impedance is the maximum in one pulse period. In this case, since the amount of variation of the impedance affected by blood can be broadly captured, the SN ratio is enhanced, whereby highly accurate measurement is made possible.

Furthermore, in this case or in the second embodiment, the first analyzing unit may preferably output the average of the first difference value as the first variation amount, and the second analyzing unit may preferably output the average of the second difference value as the second variation amount. In this case, an index indicating the component of blood is generated based on the average value of the variation amount of impedance. Therefore, even if the pulse suddenly fluctuates, the effects of this fluctuation can be minimized.

Furthermore, in the above biometric measurement apparatus, when the first variation amount is $\Delta Z_L$, when the second variation amount is $\Delta Z_H$, and when the index is hematocrit Hct, the index generator may generate the index by calculating $Hct = 1 - (\Delta Z_H / \Delta Z_L)$. In this case, hematocrit can be measured without the need to draw blood.

DETAILED DESCRIPTION OF PREFERRED EMBODIMENTS

1. Principle for Calculating Hematocrit

Before describing an embodiment of the present invention, description will be given of a principle of a method for calculating hematocrit without drawing blood from a human body.

Figure 1:
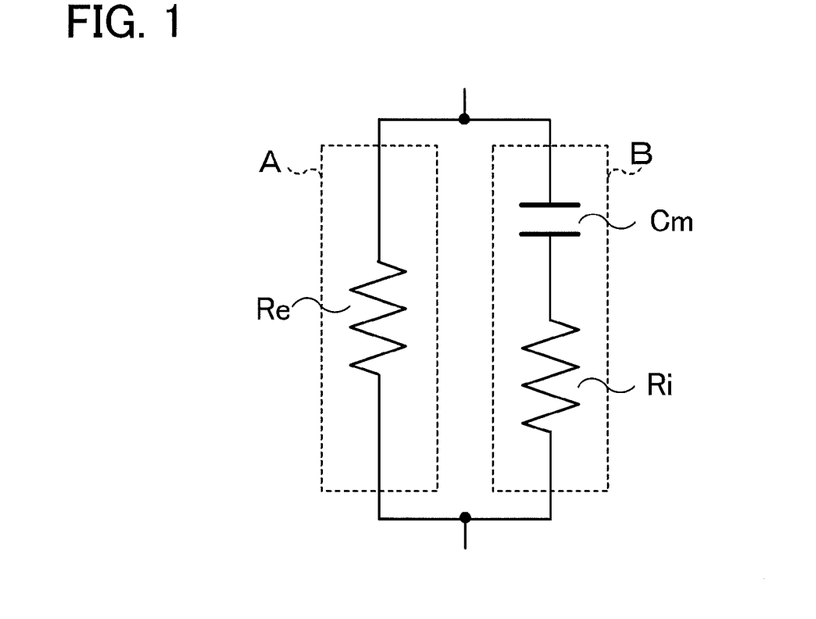
FIG. 1 is a circuit diagram showing an equivalent circuit of the blood.

FIG. 1 shows an equivalent circuit of the blood. Blood may be broadly divided into blood plasma A and red blood cells B. The blood plasma A is the electrolyte part of the blood from which red blood cells and the like are removed. On the other hand, red blood cells B are formed by enclosing hemoglobin and the like by red blood cell membranes. Blood plasma A can be expressed by resistance Re, and red blood cells B can be expressed by capacitance Cm and resistance Ri in series.

Figure 2:
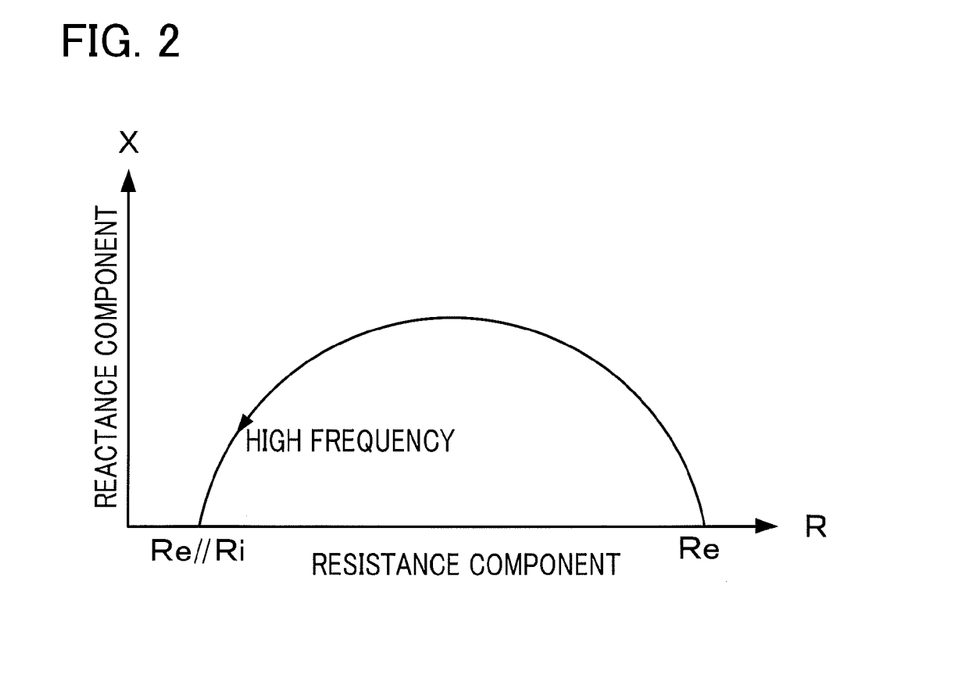
FIG. 2 is a graph showing the change in the impedance of the blood depending on a frequency, the change shown by the reactance component and the resistance component.

According to this equivalent circuit, the impedance of capacitance Cm becomes larger when the frequency is low, and the current flows only through blood plasma A. Accordingly, resistance Re is dominant in the impedance of blood. On the other hand, the impedance of capacitance Cm becomes smaller when the frequency is high, and the current flows through blood plasma A and red blood cells B. Accordingly, the impedance of blood is nearly a parallel of resistance Re and Ri. FIG. 2 is a graph showing the change in the impedance of blood depending on a frequency, the change shown by reactance component and resistance component.

Hematocrit is the proportion of blood volume that is occupied by blood cells. When the amount of blood is Vb, when the amount of blood plasma is Vp, and when the amount of red blood cell is Vq, hematocrit Hct is given in accordance with the following Equation 1.

$$Hct = Vq/Vb = (Vb - Vp)/Vb = 1 - Vp/Vb \qquad \text{Equation 1}$$

When the area of the blood is S, when the length is L, and when the volume is Vb, the relationship between resistivity pb (that is, rho b) and impedance $Z_H$ is given in accordance with the following Equation 2.

$$S*L = Vb = \rho b * L^2 / Z_H \qquad \text{Equation 2}$$

Furthermore, when the area of blood plasma is S, when the length is L, and when the volume is Vp, the relationship between resistivity ρp (that is, rho p) and impedance $Z_L$ is given in accordance with the following Equation 3.

$$S*L = Vp = \rho p * L^2 / Z_L \qquad \text{Equation 3}$$

Equation 4 can be derived by combining Equation 2 and Equation 3 into Equation 1 and taking into account that the resistivity of the intracellular fluid and that of red blood cells are almost equal.

$$Hct = 1 - (\rho p / \rho b)(Z_H / Z_L) = 1 - (Z_H / Z_L) \qquad \text{Equation 4}$$

As described above, the impedance of blood plasma can be obtained by measuring the impedance of blood with a low frequency, and the impedance of blood can be measured with a high frequency. Therefore, hematocrit can be calculated in accordance with Equation 4 if the impedance of blood is measured with a low frequency and with a high frequency.

However, measuring the impedance of blood requires either drawing blood from the body or inserting a tube into the body, both of which are accompanied by pain. The hematocrit is used as an index for anemia, but drawing blood is undesirable because it aggravates the symptoms of anemia.

Accordingly, the present invention focuses on the variation in bioelectric impedance synchronized with a pulse wave so that the information about the blood can be captured without drawing blood. For example, the bioelectric impedance is obtained by causing the current to flow from the toe to the heel of the sole of a foot and observing the voltage between a pair of voltage electrodes (input electrodes) arranged on a portion of the sole at which the artery runs through.

Figure 3:
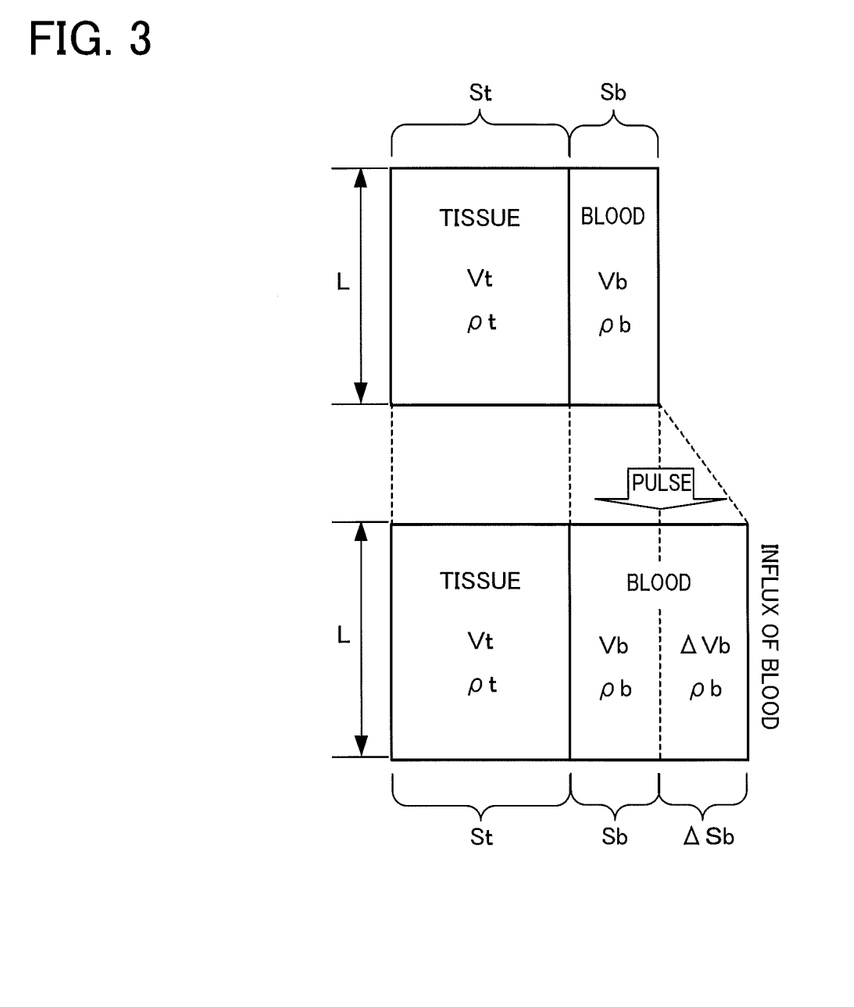
FIG. 3 is an explanatory diagram for describing the influx of the blood into tissues and the pulse.

In this case, under an area between a pair of voltage electrodes are the tissues and the blood shown in FIG. 3. When a pulsation takes place, the blood flows into the tissues. Conditions change from those as shown in the upper portion of FIG. 3 to those as shown in the lower portion of FIG. 3. As is obvious from FIG. 3, the tissue volume Vt and the resistivity ρt (that is, rho t) do not change before and after the influx of blood. What has changed is the volume of blood that has increased by ΔVb due to the influx of blood. In other words, the changed amount of the bioelectric impedance corresponds to the changed amount of blood ΔV.

In FIG. 3, when the area S, the length L, and volume V are provided, the relationship between resistivity ρ (rho) and impedance Z is given in accordance with the following Equation 5.

$$S*L=V=\rho*L^2/Z \quad \text{Equation 5}$$

Because the positions of electrodes are fixed,
S∝V∝(ρ/Z)=ρY (S is proportional to V; V is proportional to ρ/Z; and ρ/Z is equal to ρY (that is, rho Y).)

$$Y=V/\rho$$

where Y is admittance. Provided that the changed amount of admittance is ΔY, the following is true.

$$\Delta Y = (Vt/\rho t + (Vb/\rho b + \Delta Vb/\rho b)) - (Vt/\rho t + Vb/\rho b)$$
$$= \Delta Vb/\rho b$$

Then, the following Equation 6 is true.

$$1/\Delta Z = \Delta Vb/\rho b$$
$$\Delta Z = \rho b/\Delta Vb \quad \text{Equation 6}$$

In Equation 6, ΔZ is the variation amount in the bioelectric impedance of a portion of the sole at which the artery runs through. This is the amount of variation in the bioelectric impedance of the tissues and the blood. As shown in FIG. 3, the amount of variation merely arises from blood, and the component of tissue is not reflected therein.

Accordingly, measuring the amount of variation in bioelectric impedance between different parts (two points) of a living body, it is possible to obtain only the amount of variation in the bioelectric impedance of blood. This is apparent from Equation 6.

On the other hand, hematocrit Hct can be obtained, as shown in Equation 4, based on the ratio between the bioelectric impedance $Z_H$ of blood at a high frequency and the bioelectric impedance $Z_L$ of blood at a low frequency. As described above, the bioelectric impedance of blood can be obtained based on the amount of variation of bioelectric impedance between different parts of a living body.

Therefore, in cases in which the amount of variation of bioelectric impedance between different parts of a living body at a low frequency is $\Delta Z_L$, and in which the amount of variation of bioelectric impedance between different portions of a living body at a high frequency is $\Delta Z_H$, hematocrit Hct is given in accordance with the following Equation 7.

$$Hct=1-(\Delta Z_H/\Delta Z_L) \quad \text{Equation 7}$$

This means that hematocrit Hct can be obtained based on the ratio between $\Delta Z_L$ and $\Delta Z_H$. Therefore, hematocrit Hct can be measured without drawing the blood from the body.

2. First Embodiment

Figure 4:
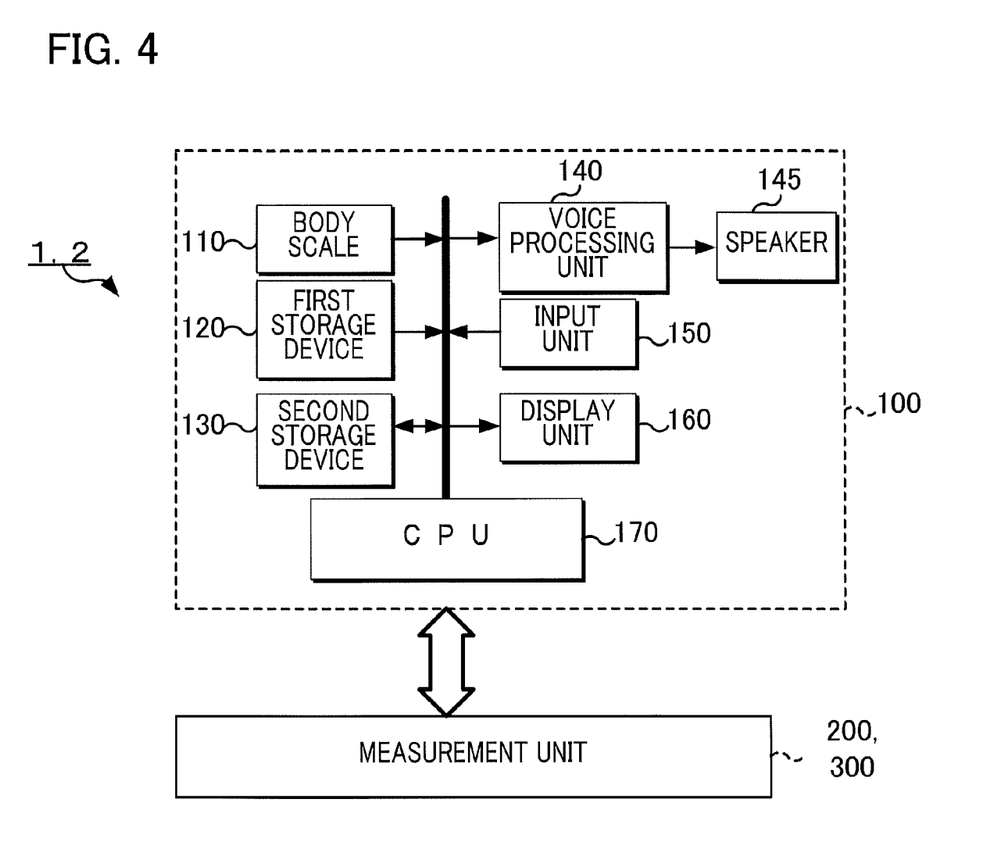
FIG. 4 is a block diagram showing a configuration of biometric measurement apparatuses 1 and 2.

FIG. 4 is a block diagram showing a configuration of a biometric measurement apparatus 1 according to a first embodiment of the present invention. This biometric measurement apparatus 1 is for measuring conditions of a living body such as weight, a body fat percentage, hematocrit, and the like.

Biometric measurement apparatus 1 has a management unit 100 for measuring weight and for managing operations of the whole apparatus and a measurement unit 200 for measuring the bioelectric impedance and the hematocrit of different parts of a human subject. Management unit 100 has a body scale 110, a first storage device 120, a second storage device 130, a voice processing unit 140, a speaker 145, an input unit 150, and a display unit 160. These components are connected to a CPU (Central Processing Unit) 170 via a bus. CPU 170 serves as a control center for controlling the entire apparatus. CPU 170 operates by receiving a supply of clock signals from a clock signal generating circuit (not shown). Furthermore, when a power source switch (not shown) is turned on, power from a power source is provided by a power source circuit.

Body scale 110 measures the weight of a human subject, to output weight data to CPU 170 via a bus. First storage device 120 is a non-volatile memory storage device and is configured, for example, by a ROM (Read Only Memory). First storage device 120 has stored therein a control program for controlling the entire apparatus. CPU 170 controls each unit in accordance with the control program.

Second storage device 130 is a volatile memory device and is configured, for example, by a DRAM (Dynamic Random Access Memory) and the like. Second storage device 130 serves as a work area of CPU 170, and stores data when CPU 170 executes a predetermined calculation. Furthermore, voice processing unit 140, under the control of CPU 170, amplifies a voice signal obtained by DA converting voice data, for output to speaker 145. Speaker 145 emits sound by converting amplified voice signal to vibration, whereby a variety of information can be given to a human subject.

Input unit 150 is configured of various types of switches, and when a human subject operates a switch, information such as height, age, and sex is input. Display unit 160 has a function of displaying a measurement result such as weight, body fat, or hematocrit, or a message prompting a human subject to input various pieces of information. Display unit 160 is formed, for example, by a liquid crystal display device. Measurement unit 200 measures bioelectric impedance and the like under the control of CPU 170.

Figure 5:
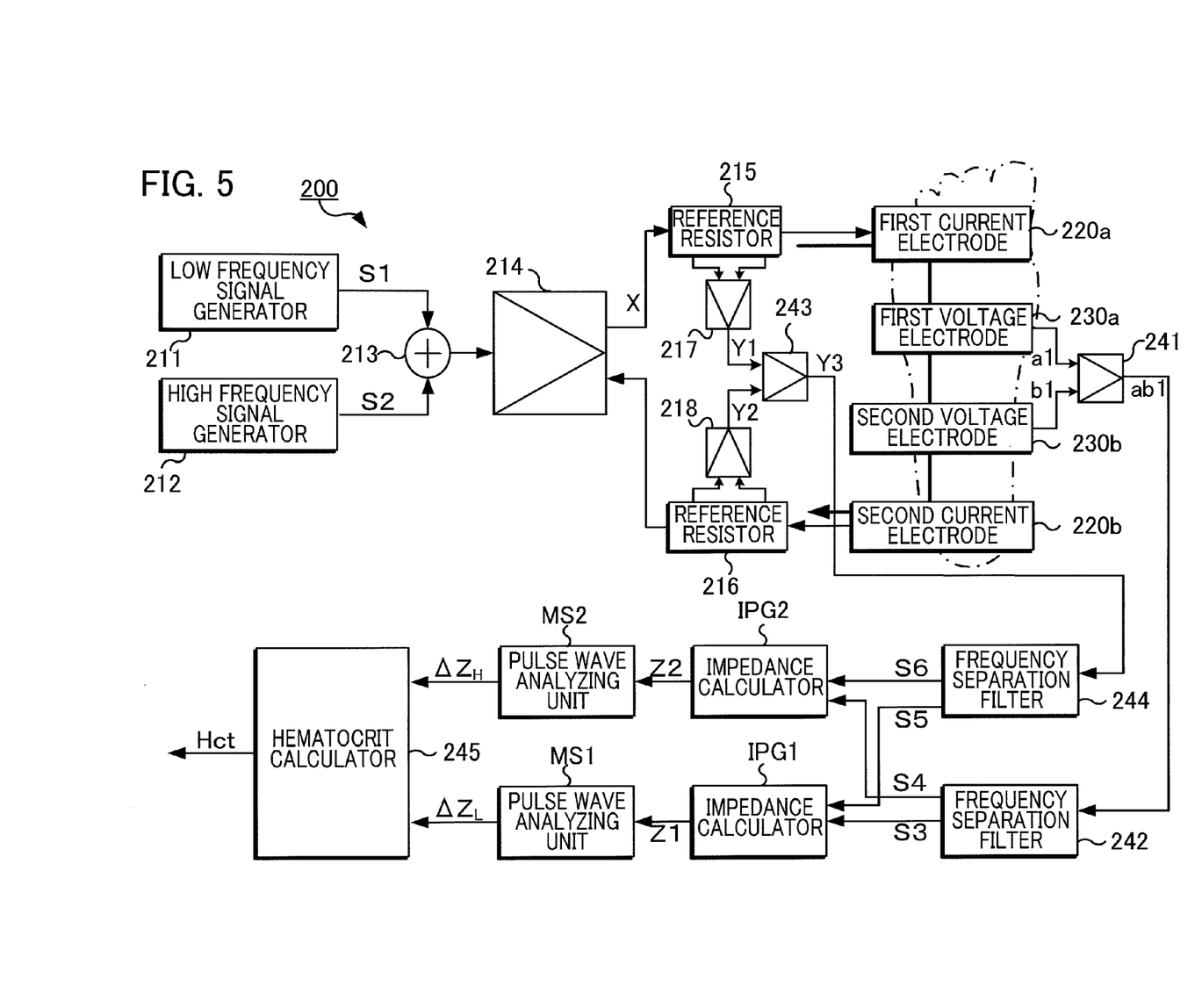
FIG. 5 is a block diagram showing a configuration of a measurement unit 200.

As shown in FIG. 5, measurement unit 200 has a low frequency signal generator 211 for generating a first signal S1 and a high frequency signal generator 212 for generating a second signal S2. The first signal S1 and the second signal S2 each are sine wave signals. The frequency 2 of the second signal S2 is higher than the frequency f1 of the first signal S1. For example, the frequency f1 of the first signal S1 is 5 KHz, and the frequency f2 of the second signal S2 is 20 MHz. The settings of a low frequency and a high frequency are selected so that hematocrit can be measured, which will be described later.

Adder 213 adds the first signal S1 and the second signal S2. Adder 213 has a function of frequency multiplexing by multiplexing signals of two frequencies. The output signal from adder 213 is supplied, via an amplifier circuit 214 for outputting a signal of a differential mode, to a first current electrode 220a and a second current electrode 220b.

A signal X output via first current electrode 220a and second current electrode 220b is a constant voltage signal, but it may be a constant current signal. However, in reality, because it is not easy to drive a signal having a frequency component of 20 MHz with a constant current, it is preferable to drive a signal with the constant voltage.

Measurement unit 200 has a first voltage electrode 230a, a second voltage electrode 230b, and a differential amplifier circuit 241. Differential amplifier circuit 241 amplifies input signals a1, b1 supplied from first voltage electrode 230a and second voltage electrode 230b, to generate an output signal ab1. Because the output signal X supplied to a living body via first current electrode 220a and second current electrode 220b is of constant voltage, the input signals a1 and b1 are given in the form of current. If the output signal X is of constant current, the input signals a1 and b1 are given in the form of voltage.

Thus, first current electrode 220a and second current electrode 220b serve as a pair of output electrodes, and first voltage electrode 230a and second voltage electrode 230b serve as a pair of input electrodes. The form of signals output from the output electrodes and the form of signals input to the input electrodes may be either current or voltage.

The output signal ab1 of differential amplifier circuit 241 is a frequency-multiplexed signal. A frequency separation filter 242 is used for frequency-separating (demultiplexing) the output signal from differential amplifier circuit 241. This frequency separation filter 242 may be configured of a low pass filter that passes frequency f1 and attenuates frequency f2 and a high pass filter that passes frequency f2 and attenuates frequency f1, or may be configured of a band-pass filter that extracts the frequency f1 components and a band-pass filter that extracts the frequency f2 components.

Frequency separation filter 242 outputs a third signal S3 corresponding to frequency f1 and a fourth signal S4 corresponding to frequency f2. Both signals are signals indicating the voltage value between first voltage electrode 230a and second voltage electrode 230b. The third signal S3 indicates a voltage value corresponding to frequency f1, and the fourth signal S4 indicates a voltage value corresponding to frequency f2.

Furthermore, measurement unit 200 is further provided with reference resistors 215 and 216 and differential amplifier circuits 217, 218 and 243. Reference resistor 215 is inserted between amplifier circuit 214 and first current electrode 220a; and reference resistor 216 is inserted between second current electrode 220b and amplifier circuit 214. Differential amplifier circuit 217 amplifies input signals supplied from both ends of reference resistor 215, to generate an output signal Y1; and differential amplifier circuit 218 amplifies input signals supplied from both ends of reference resistor 216, to generate an output signal Y2. These output signals Y1 and Y2 are out of phase by 180 degrees, and the signal levels are inverted. Differential amplifier circuit 243 generates the difference between signals Y1 and Y2 supplied from differential amplifier circuits 217 and 218 as an output signal Y3. As a result, the amplitude of an output signal from differential amplifier circuit 243 can be increased.

The output signal Y3 from differential amplifier circuit 243 is a frequency-multiplexed signal. A frequency separation filter 244 is used for frequency-separating the output signal Y3 output from differential amplifier circuit 243, and the configuration thereof is the same as frequency separation filter 242. Frequency separation filter 244 outputs a fifth signal S5 corresponding to frequency f1 and a sixth signal S6 corresponding to frequency f2. Both signals are signals indicating a current value between first voltage electrode 230a and second voltage electrode 230b. Fifth signal S5 indicates a current value corresponding to frequency f1, and sixth signal S6 indicates a current value corresponding to frequency f2.

A reference resistor is inserted both between amplifier circuit 214 and first current electrode 220a and between second current electrode 220b and amplifier circuit 214 to increase an SN ratio for enhancing the accuracy in measuring a current value. If there is no such a need, a reference resistor may be inserted in either one. In this case, either differential amplifier circuit 217 or 218 is no longer required.

In measurement unit 200, a calculator including impedance calculators IPG1 and IPG2, pulse wave analyzing units MS1 and MS2, and a hematocrit calculator 245 uses third signal S3, fourth signal S4, fifth signal S5 and sixth signal S6, to calculate hematocrit Hct. This calculator may be configured by hardware, but in the present embodiment, is configured by a DSP (Digital Signal Processor) and a computer program thereof. Hematocrit Hct is generated based on the bioelectric impedance at frequency f1 and the bioelectric impedance at frequency f2.

The bioelectric impedance may be measured using any method. The method of measurement is broadly divided into an analog method and a digital method. According to an analog method, for example, a third signal S3, a fourth signal S4, and a fifth signal S5, and a sixth signal S6 each are full-wave rectified, and the results thereof are averaged, to calculate impedance. Furthermore, another analog method detects the peak of a sine wave, to calculate impedance based on the detected peak value. In any method, distortion due to a high-frequency signal processing is problematic.

On the other hand, the digital methods include a method in which undersampling and DFT (Discrete Fourier Transform) are combined, a method in which high speed sampling and DFT are combined, and a method of detecting the peak that is in synchronization with a sine wave. The method in which high speed sampling and DFT are combined requires an AD converter of extremely high speed because fourth signal S4 and sixth signal S6 must be sampled at a frequency of twice as much as frequency f2 or higher. On the other hand, the detection of the peak that is in synchronization with a sine wave requires accurate detection of the peak, which, however, is difficult.

Accordingly, the present embodiment uses a method in which undersampling and DFT are combined. Impedance calculators IPG1 and IPG2 obtain bioelectric impedance by calculation.

Figure 6:
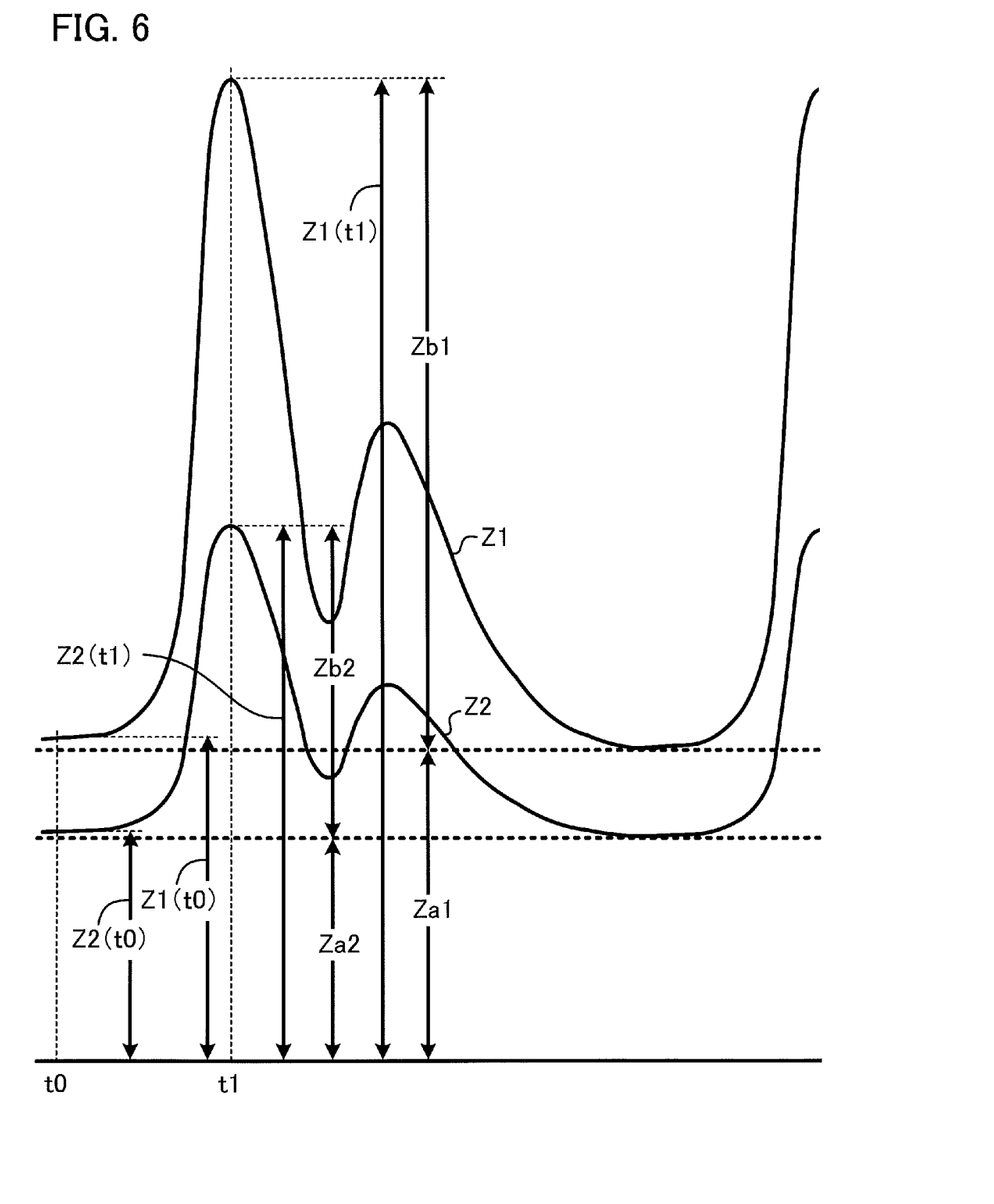
FIG. 6 is a waveform diagram showing an example of bioelectric impedance that varies depending on a pulse.

Looking at the bioelectric impedance in a short period, the bioelectric impedance varies in synchronization with a pulse. Impedance calculator IPG1 calculates bioelectric impedance Z1 at frequency f1 based on third signal S3 and fifth signal S5, the impedance Z1 varying in synchronization with a pulse, and impedance calculator IPG2 calculates bioelectric impedance Z2 at frequency f2 based on fourth signal S4 and sixth signal S6, the impedance Z2 varying in synchronization with a pulse. FIG. 6 shows an example of bioelectric impedance Z1 and Z2 that change in synchronization with a pulse.

As shown in FIG. 6, bioelectric impedance Z1 at low frequency f1 can be represented by the sum of Za1 and Zb1. Considering that bioelectric impedance is broadly divided into tissues and blood, Za1 is the bioelectric impedance of tissues at low frequency f1, and Zb1 is the bioelectric impedance of blood at low frequency f1. On the other hand, Za2 is bioelectric impedance of tissues at high frequency f2, and Zb2 is the bioelectric impedance of blood at high frequency f2. Furthermore, Zb1 represents impedance corresponding to blood plasma of blood, and Zb2 represents impedance of whole blood including blood plasma and red blood cells.

Za1 and Za2 are not equal because a cell making up tissues can be also represented by a series of capacitance and resistance in the same way as red blood cells. In other words, Z1 is the bioelectric impedance of extracellular fluid (interstitial fluid) as when the amount of blood that has flowed into tissues by pulsation is minimum, and Z2 is the bioelectric impedance of extracellular fluid and cells (intracellular fluid) as when the amount of blood that has flowed into tissue by pulsation is minimum. Therefore, Za2 is smaller than Za1 by the amount corresponding to the cells.

Pulse wave analyzing units MS1 and MS2 execute analysis of a pulse wave for bioelectric impedance Z1 and Z2, to identify Zb1 and Zb2. Specifically, Z1 at time t0 (hereinafter, Z1(t0)), Z2 at time t0 (hereinafter, Z2(t0)), Z1 at time t1 (hereinafter, Z1(t1)), and Z2 at time t1 (hereinafter, Z2(t1)) are obtained. In this example, a timing at which the pulse wave is the minimum is t0, and a timing at which the pulse wave is the maximum is t1. Thus determining t0 and t1, it is possible to extract Zb1 and Zb2 with large amplitude. Accordingly, the SN ratio is increased, and the accuracy in measurement can be enhanced. The timings for the minimum and the maximum can be identified by storing Z1 and Z2 only for one pulse wave, to search in the stored data. However, the timings t0 and t1 do not necessarily correspond to the timing of the minimum and the maximum of a pulse wave.

Pulse wave analyzing unit MS1 calculates the difference between Z1(t1) at time t1 and Z1(t0) at time t0 as a first difference value, for output as first variation amount $\Delta Z_L$. Furthermore, pulse wave analyzing unit MS2 calculates the difference between Z2(t1) at time t1 and Z2(t0) at time t0 as a second difference value, for output as second variation amount $\Delta Z_H$ $$\Delta Z_L = Z1(t1) - Z1(t0)$$

$$\Delta Z_H = Z2(t1) - Z2(t0)$$

In other words, pulse wave analyzing units MS1 and MS2 calculate, for each of bioelectric impedance Z1 and Z2, the difference between a timing (t0) and another timing (t1). $\Delta Z_H$ corresponds to the impedance of blood, and $\Delta Z_L$ corresponds to the impedance of blood plasma.

Hematocrit calculator 245 computes $Hct=1-(\Delta Z_H/\Delta Z_L)$ as shown in the above Equation 7, to calculate hematocrit Hct.

As has been described in the foregoing, according to the present embodiment, hematocrit Hct can be measured without drawing blood from a human body.

In the present embodiment, because a first process of measuring bioelectric impedance Z1 at frequency f1 and a second process of measuring bioelectric impedance Z2 at frequency f2 are executed simultaneously, the configuration is comprehensive. However, it is possible to measure hematocrit Hct even without executing the first process and the second process simultaneously. Description will be now given of a second embodiment in which the configuration is simplified by executing the first process and the second process at different times.

3. Second embodiment

Figure 7:
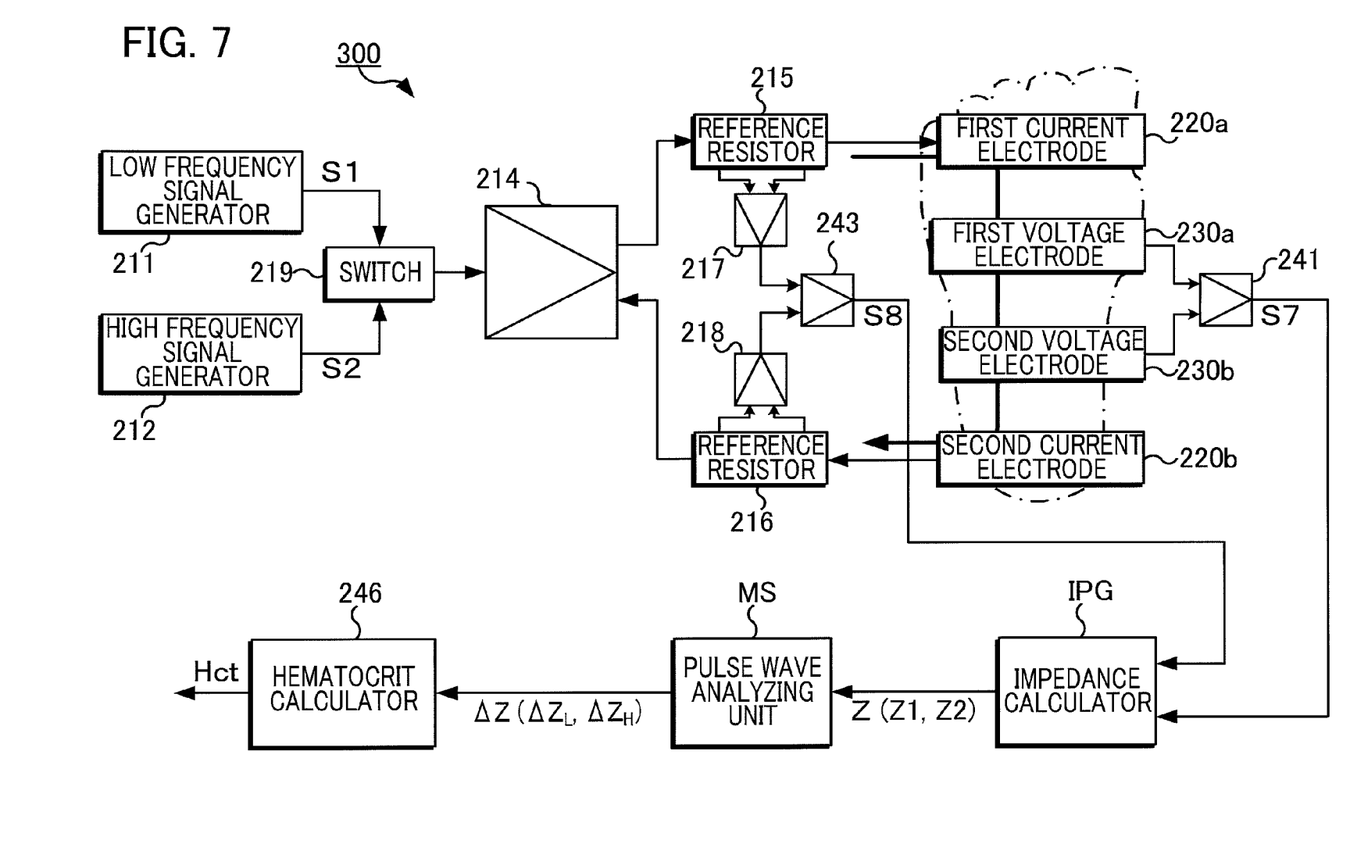
FIG. 7 is a block diagram showing a configuration of a measurement unit 300.

A configuration of a biometric measurement apparatus 2 according to a second embodiment of the present invention is as shown in FIG. 4. However, this biometric measurement apparatus 2 has a measurement unit 300 instead of measurement unit 200. Measurement unit 300 differs from measurement unit 200, as shown in FIG. 7, in that frequency separation filters 242 and 244 are not provided, in that a switch 219 and a hematocrit calculator 246 are provided instead of adder 213 and hematocrit calculator 245, respectively, in that an impedance calculator IPG is provided instead of impedance calculators IPG1 and IPG2, and in that a pulse wave analyzing unit MS is provided instead of pulse wave analyzing unit MS1 and MS2.

Switch 219 alternately switches first signal S1 and second signal S2 at time T interval, for supply to amplifier circuit 214. In other words, according to the present embodiment, frequency f1 and frequency f2 are not simultaneously multiplexed but are divided temporally (time division). Therefore, in measurement unit 300, a first process of measuring bioelectric impedance at frequency f1 and a second process of measuring bioelectric impedance at frequency f2 are performed alternately at time T interval.

For example, an output signal S7 of differential amplifier circuit 241 is a signal which alternately switches to a signal indicating a voltage value corresponding to frequency f1 or to a signal indicating a voltage value corresponding to frequency f2 at time T interval. An output signal S8 from differential amplifier circuit 243 is a signal which alternately switches to a signal indicating a current value corresponding to frequency f1 or to a signal indicating a current value corresponding to frequency f2 at time T interval. The time T needs to be at least one pulse period long. Because the average pulse rate of a human at rest is generally from 50 to 90 beats, time T is a fixed length equal to or longer than 0.8 seconds in the present embodiment. However, it is not limited to the time length of 0.8 seconds or longer or a fixed length. For example, the pulse rate is measured, and the time T may be determined based on the measured pulse rate so that the time T is one pulse period or longer. Alternatively, switch 219 may be controlled to switch in synchronization with a pulse.

In measurement unit 300, a calculator including impedance calculator IPG, pulse wave analyzing unit MS, and hematocrit calculator 246 calculates hematocrit Hct using seventh signal S7 and eighth signal S8. This calculator may be configured by hardware, but is configured by a DSP and a computer program therefor in the same ways as in the first embodiment. Furthermore, when this calculator measures bioelectric impedance, a freely selected one of the above-described methods can be used as a general rule. However, in the present embodiment, as in the first embodiment, a method in which undersampling and DFT are combined is used, with use of which impedance calculator IPG measures bioelectric impedance.

Figure 8:
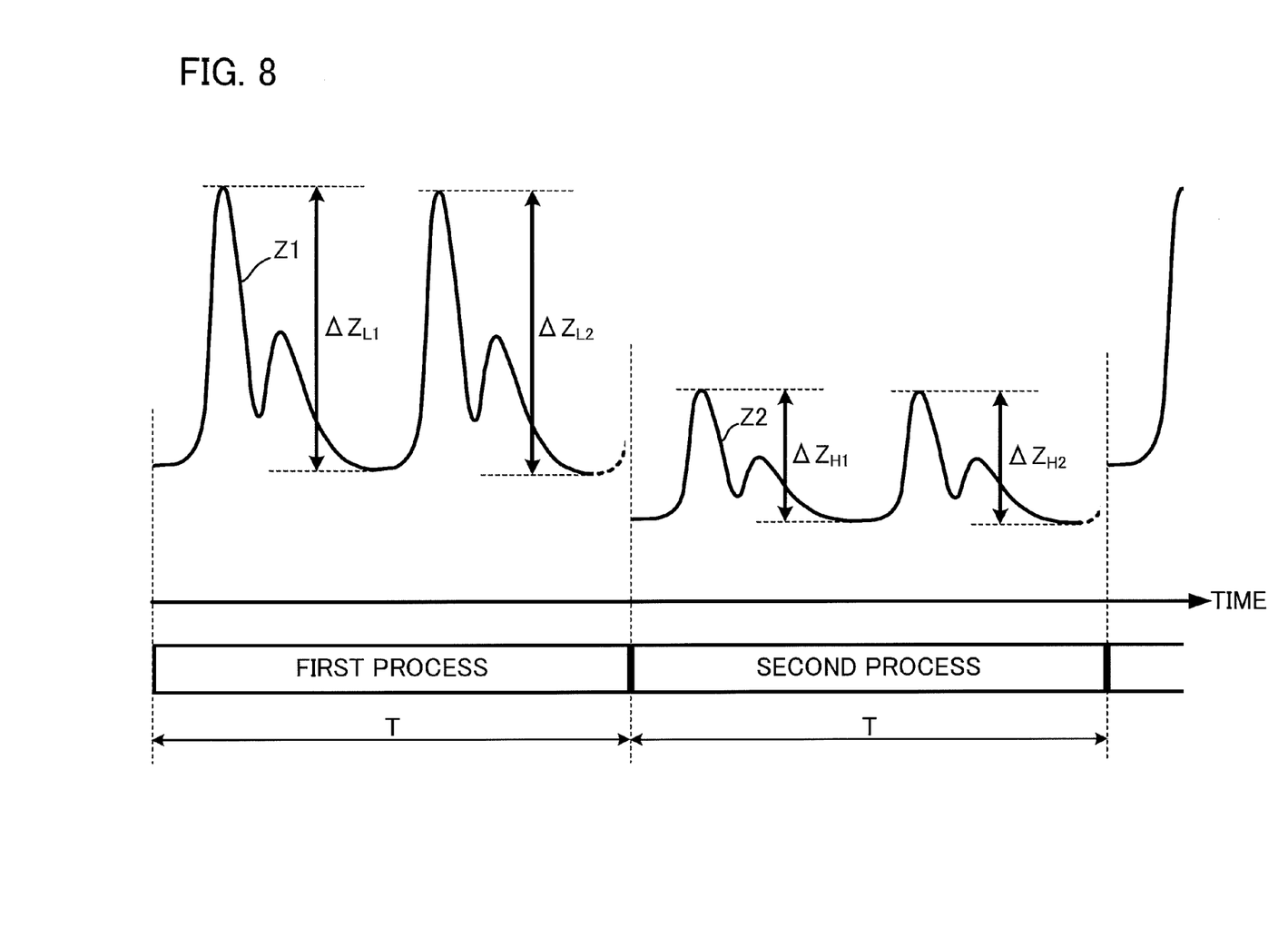
FIG. 8 is a waveform diagram showing another example of bioelectric impedance that varies depending on a pulse.

Impedance calculator IPG calculates bioelectric impedance based on seventh signal S7 and eighth signal S8. FIG. 8 shows an example of calculated bioelectric impedance. As shown in the figure, in the first process, seventh signal S7 is a signal indicating a voltage value corresponding to frequency f1. Therefore, bioelectric impedance Z1 at frequency f1 is calculated, the impedance Z1 varying in synchronization with a pulse. In the second process, eighth signal S8 is a signal indicating a current value corresponding to frequency f2. Therefore, bioelectric impedance Z2 at frequency f2 is calculated, the impedance Z2 varying in synchronization with a pulse.

Pulse wave analyzing unit MS executes the analysis of a pulse wave for bioelectric impedance Z1 calculated by impedance calculator IPG in time T for the first process, to calculate first variation amount $\Delta Z_L$, and executes the analysis of a pulse wave for bioelectric impedance Z2 calculated by impedance calculator IPG in time T for the second process, to calculate the second variation amount $\Delta Z_H$. Methods of calculating the first and second variation amount includes, for example, a first method of obtaining the difference between the maximum and the minimum values of bioelectric impedance in one pulse period and a second method of performing frequency analysis of bioelectric impedance to obtain the intensity of the maximum spectrum corresponding to a pulse.

The first method is used in the present embodiment. Pulse wave analyzing unit MS calculates the difference (first difference value) between the maximum and the minimum values of bioelectric impedance Z1 in one pulse period, for output as $\Delta Z_L$, and calculates the difference (second difference value) between the maximum and the minimum values of bioelectric impedance Z2 in one pulse period, for outputs $\Delta Z_H$. However, in the present embodiment, plural cycles of pulses can be included during time T as shown in FIG. 8. In this case, pulse wave analyzing unit MS obtains, for respective plural cycles for the first process, first difference values $\Delta Z_{L1}, \Delta Z_{L2}, \ldots$, and calculates the average of these first difference values, for use as $\Delta Z_L$. Pulse wave analyzing unit MS additionally obtains, for respective plural cycles for the second process, second difference value $\Delta Z_{H1}, \Delta Z_{H2}, \ldots$, and calculates the average of these second difference values, for use as $\Delta Z_H$.

On the other hand, in a case in which the second method is used, pulse wave analyzing unit MS performs frequency analysis of bioelectric impedance Z1, to obtain the intensity of the maximum spectrum corresponding to a pulse, for output as $\Delta Z_L$, and performs frequency analysis of bioelectric impedance Z2, to obtain the intensity of the maximum spectrum corresponding to a pulse, for output as $\Delta Z_H$. The frequency components of a pulse wave include not only a fundamental wave component but also harmonic components. The maximum spectrum corresponds to the fundamental wave component. To prevent malfunction due to noise contamination, pulse wave analyzing unit MS may preferably execute a process of attenuating high frequency components. Because the pulse rate of a human at rest is generally from 50 to 90 beats, as described above, in this process, it is preferable to have frequencies from about 0.8 Hz to about 1.5 Hz pass and to attenuate other frequencies. By frequency-analyzing a signal that has gone through such a process, it is possible to remove noise and to obtain the intensity of the maximum spectrum.

Hematocrit calculator 246, as hematocrit calculator 245 does, calculates Hct=$1-(\Delta Z_H/\Delta Z_L)$, to obtain hematocrit Hct. In the present embodiment, since a timing at which $\Delta Z_L$ is output from pulse wave analyzing unit MS and a timing at which $\Delta Z_H$ is output are not the same, hematocrit calculator 246 has a memory device for temporarily storing $\Delta Z_L$ or $\Delta Z_H$.

Thus, according to the present embodiment, hematocrit Hct can be measured without drawing blood from the body.

4. Other Features

The influx amount of blood into tissues can vary depending on a pulse period. Therefore, in view of measuring hematocrit Hct at a high level of accuracy, the first embodiment of simultaneously executing a first process of measuring bioelectric impedance Z1 at frequency f1 and a second process of measuring bioelectric impedance Z2 at frequency f2 has an advantage over the second embodiment of executing the first process and the second process at different times. Additionally, in the first embodiment, pulse wave analyzing unit MS1 outputs the difference between Z1 at time t0 and Z1 at time t1 as $\Delta Z_L$, and pulse wave analyzing unit MS2 outputs the difference between Z2 at time t0 and Z2 at time t1 as $\Delta Z_H$. In other words, hematocrit Hct is measured by calculation based on the ratio of amount of variation in impedance at the same timing. Furthermore, because time t0 is a time point at which Z1(Z2) is the smallest in one pulse period, and because time t1 is a time point at which Z1(Z2) is the greatest in one pulse period, the SN ratio increases. Therefore, according to the first embodiment, measurement with extremely high accuracy is enabled.

On the other hand, according to the second embodiment, the average of first difference values is $\Delta Z_L$, and the average of second difference values is $\Delta Z_H$. Therefore, even when a pulse suddenly fluctuates, the effect of this fluctuation can be minimized. The first embodiment may be modified so that pulse wave analyzing unit MS1 outputs the average of first difference values as the first variation amount and that pulse wave analyzing unit MS2 outputs the average of second difference values as the second variation amount.

In each of the above embodiments, hematocrit Hct was taken as an example as an index indicating the components of blood; however, the present invention is not limited thereto. For example, it may be an index such as $(\Delta Z_H/\Delta Z_L)$. Both hematocrit Hct and $(\Delta Z_H/\Delta Z_L)$ can be used as an index showing the degree of anemia.

Furthermore, when measuring a condition of a living body such as body fat percentage, and when one frequency is used to measure bioelectric impedance, this frequency is made the same as low frequency f1, so that signal S3 is integrated to obtain the average value of bioelectric impedance. This value can be used for generating at CPU 170 an index showing the conditions of a living body such as body fat percentage. In this case, the apparatus can be simplified because the configuration can be used for both purposes, and hematocrit Hct and the condition of a living body such as body fat percentage can be measured simultaneously.

What is claimed is:

1. A biometric measurement apparatus comprising:
    an impedance measurer for measuring the impedance of tissues and blood in a living body with a first frequency, for output as a first impedance, and for measuring the impedance of tissues and blood of the living body with a second frequency, the second frequency higher than the first frequency, for output as a second impedance, the impedance measurer having output electrodes and input electrodes that are in contact with the surface of the body during the measurement;
    a first analyzing unit for analyzing variation in the first impedance, to output as a first variation amount;
    a second analyzing unit for analyzing variation in the second impedance, to output as a second variation amount;
    an index generator for generating an index indicating a component of the blood based on the ratio between the first variation amount and the second variation amount; and
    wherein the first variation amount is $\Delta Z_L$, the second variation amount is $\Delta Z_H$, and the index is hematocrit Hct, and wherein the index generator generates the index by calculating the equation Hct=$1-(\Delta Z_H/\Delta Z_L)$.

2. A biometric measurement apparatus according to claim 1,
    wherein the impedance measurer executes a first process of measuring the first impedance with the first frequency and a second process of measuring the second impedance with the second frequency simultaneously.

3. A biometric measurement apparatus according to claim 2,
    wherein the first analyzing unit outputs, as the first variation amount, a first difference value that is the difference between the first impedance of a first time point and the first impedance of a second time point, and
    wherein the second analyzing unit outputs, as the second variation amount, a second difference value that is the difference between the second impedance of the first time point and the second impedance of the second time point.

4. A biometric measurement apparatus according to claim 3,
    wherein the first impedance varies in synchronization with a pulse,
    wherein the first time point is a time point at which the first impedance is the minimum in one pulse period, and
    wherein the second time point is a time point at which the first impedance is the maximum in one pulse period.

5. A biometric measurement apparatus according to claim 2, wherein the impedance measurer comprises:

a first frequency generator for generating a first signal of the first frequency;

a second frequency generator for generating a second signal of the second frequency;

a frequency multiplexer for frequency-multiplexing the first signal and the second signal to obtain an output signal for supply to the output electrodes;

a frequency separator for demultiplexing an input signal obtained through the input electrodes into a third signal having the first frequency and a fourth signal having the second frequency;

a first generator for outputting the first impedance based on the third signal; and a second generator for outputting the second impedance based on the fourth signal.

6. A biometric measurement apparatus according to claim 5, wherein the first analyzing unit outputs, as the first variation amount, a first difference value that is the difference between the first impedance of a first time point and the first impedance of a second time point, and wherein the second analyzing unit outputs, as the second variation amount, a second difference value that is the difference between the second impedance of the first time point and the second impedance of the second time point.

7. A biometric measurement apparatus according to claim 6, wherein the first impedance varies in synchronization with a pulse, wherein the first time point is a time point at which the first impedance is the minimum in one pulse period, and wherein the second time point is a time point at which the first impedance is the maximum in one pulse period.

8. A biometric measurement apparatus according to claim 7, wherein the first analyzing unit outputs the average of the first difference value as the first variation amount, and the second analyzing unit outputs the average of the second difference value as the second variation amount.

9. A biometric measurement apparatus according to claim 1, wherein the first frequency is approximately is 5 KHz, and the second frequency is approximately is 20 MHz.

10. A biometric measurement apparatus according to claim 1, comprising:

a management unit including a body scale for measuring a weight of the living body.

11. A biometric measurement apparatus according to claim 1, wherein the input electrodes are adapted to contact a portion of a sole of a foot of the living body.

12. A biometric measurement apparatus comprising:

an impedance measurer for measuring the impedance of tissues and blood in a living body with a first frequency, for output as a first impedance, and for measuring the impedance of tissues and blood of the living body with a second frequency, the second frequency higher than the first frequency, for output as a second impedance, the impedance measurer having output electrodes and input electrodes that are in contact with the surface of the body during the measurement;

an analyzing unit for analyzing variation in the first impedance, to output as a first variation amount and for analyzing variation in the second impedance, to output as a second variation amount;

an index generator for generating an index indicating a component of the blood based on the ratio between the first variation amount and the second variation amount, wherein the first variation amount is $\Delta Z_L$, the second variation amount is $\Delta Z_H$, and the index is hematocrit Hct, and wherein the index generator generates the index by calculating the equation Hct=$1-(\Delta Z_H/\Delta Z_L)$; and wherein the impedance measurer executes a first process of measuring the first impedance with the first frequency and a second process of measuring the second impedance with the second frequency at different times.

13. A biometric measurement apparatus according to claim 12, wherein the first analyzing unit outputs, as the first variation amount, a first difference value that is the difference between the maximum value and the minimum value of the first impedance in one pulse period, and wherein the second analyzing unit outputs, as the second variation amount, a second difference value that is the difference between the maximum value and the minimum value of the second impedance in one pulse period.

14. A biometric measurement apparatus according to claim 13, wherein the first analyzing unit outputs the average of the first difference value as the first variation amount, and the second analyzing unit outputs the average of the second difference value as the second variation amount.

15. A biometric measurement apparatus according to claim 12, wherein the first analyzing unit performs frequency analysis of the first impedance, to output the intensity of the maximum spectrum corresponding to a pulse as the first variation amount, and wherein the second analyzing unit performs frequency analysis of the second impedance, to output the intensity of the maximum spectrum corresponding to a pulse as the second variation amount.

16. A biometric measurement apparatus according to claim 12, wherein the first frequency is approximately is 5 KHz, and the second frequency is approximately is 20 MHz.

17. A biometric measurement apparatus according to claim 12, wherein a time period between the first impedance with the first frequency and the second impedance with the second frequency is at least one pulse period long.

18. A biometric measurement apparatus according to claim 17, wherein the at least one pulse period is equal to or greater than 0.8 seconds.

19. A biometric measurement apparatus according to claim 12, comprising:

a management unit including a body scale for measuring a weight of the living body, and wherein the input electrodes are adapted to contact a portion of a sole of a foot of the living body.

* * * * *